United States Patent [19]

Shiokawa et al.

[11] Patent Number: 4,666,503
[45] Date of Patent: May 19, 1987

[54] SUBSTITUTED PHENOXYALKANECARBOXYLIC ACID ESTERS USED TO COMBAT WEEDS IN RICE FIELDS

[75] Inventors: Kozo Shiokawa, Kawasaki; Koichi Moriya, Hachioji; Toshio Goto, Sagamihara; Atsumi Kamochi, Hino; Seishi Ito, Hachioji; Mitsugu Horita, Hino, all of Japan

[73] Assignee: Nihon Tokushu Noyaku Seizo K.K., Tokyo, Japan

[21] Appl. No.: 661,622

[22] Filed: Oct. 17, 1984

[30] Foreign Application Priority Data

Oct. 25, 1983 [JP] Japan .................. 58-198235

[51] Int. Cl.⁴ ............ A01N 43/78; A01N 43/76; A01N 43/52
[52] U.S. Cl. .................... 71/90; 71/88; 71/91; 71/92; 548/166; 548/170; 548/221; 548/337
[58] Field of Search ............ 71/88, 90, 98, 103, 71/109, 116, 124, 91; 548/170, 221

[56] References Cited

U.S. PATENT DOCUMENTS

| | | | |
|---|---|---|---|
| 4,130,413 | 12/1978 | Handte et al. | 71/88 |
| 4,182,621 | 1/1980 | Ogata et al. | 71/124 |
| 4,340,418 | 7/1982 | Eicken et al. | 71/103 |
| 4,482,373 | 11/1984 | Handte et al. | 71/88 |

FOREIGN PATENT DOCUMENTS 53-40767 4/1978 Japan .

*Primary Examiner*—Robert Gerstl
*Assistant Examiner*—Stephen M. Kapner
*Attorney, Agent, or Firm*—Sprung Horn Kramer & Woods

[57] ABSTRACT

Novel substituted phenoxyalkanecarboxylic acid esters of the formula

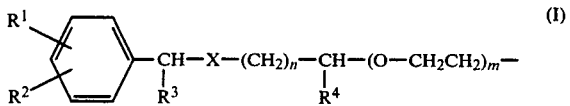

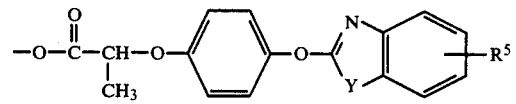

(I)

in which $R^1$ and $R^2$, independently of one another, are a hydrogen atom, a halogen atom, a lower alkyl group or a nitro group, or $R^1$ and $R^2$, together with the benzene ring to which they are bonded, are a naphthalene ring, $R^3$ and $R^4$, independently of one another, are a hydrogen atom or a methyl group, n is 1 or 2, m is 0 or 1, X is an oxygen atom, a sulfur atom, a sulfonyl group or a group of the formula

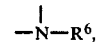

in which
$R^6$ is a lower alkyl group,
$R^5$ is a hydrogen atom or a halogen atom, and
Y is an oxygen atom or a sulfur atom,
and the use of the new compounds as herbicides.

2 Claims, No Drawings

SUBSTITUTED PHENOXYALKANECARBOXYLIC ACID ESTERS USED TO COMBAT WEEDS IN RICE FIELDS

The invention relates to certain new substituted phenoxyalkanecarboxylic acid esters, to herbicidal compositions containing such compounds and to methods for combating weeds utilizing such compounds.

It has already been disclosed that certain benzothiazolyl-oxy-phenoxy-propionates have good herbicidal properties (see U.S. Pat. No. 4,130,413 and JP-OS (Japanese Published Specification) No. 40,767-1978). Thus the ethyl-2 {4-[(6-chloro-2-benzothiazolyl)-oxy]-phenoxy}-propionate can be used for combating weeds. However, the action of this compound is not always completely satisfactory, especially when small amounts and low concentrations are applied.

The present invention now provides, as new compounds the substituted phenoxyalkanecarboxylic acid esters of the general formula

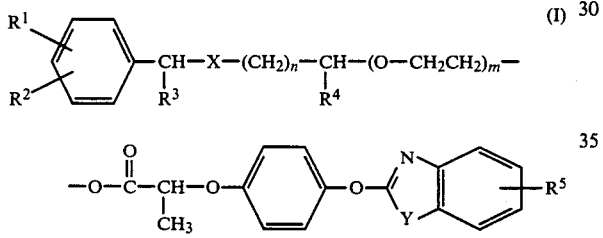

in which
R$^1$ and R$^2$, independently of one another, represent a hydrogen atom, a halogen atom, a lower alkyl group or a nitro group, or R$^1$ and R$^2$, together with the benzene ring to which they are bonded, represent a naphthalene ring,
R$^3$ and R$^4$, independently of one another, represent a hydrogen atom or a methyl group,
n represents 1 or 2,
m represents 0 or 1,
X represents an oxygen atom, a sulfur atom, a sulfonyl group or a group of the formula $$-\underset{|}{N}-R^6,$$

in which
R$^6$ represents a lower alkyl group,
R$^5$ represents a hydrogen atom or a halogen atom, and
Y represents an oxygen atom or a sulfur atom.

The substituted phenoxyalkanecarboxylic acid esters of the formula (I) contain at least one asymmetrically substituted carbon atom and can therefore occur in different enantiomeric forms. The invention relates both to the possible individual isomers and to mixtures of these isomers.

The substituted phenoxyalkanecarboxylic acid esters of the formula (I), can be prepared by a process which comprises
(a) reacting a compound of the general formula

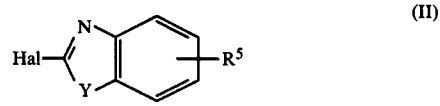

in which
R$^5$ and Y have the meanings given above and
Hal represents a halogen atom,
with a compound of the general formula

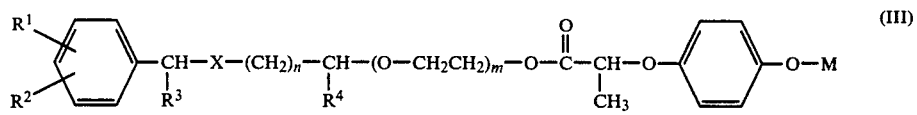

in which
R$^1$, R$^2$, R$^3$, R$^4$, m, n and X have the meanings given above and
M represents a hydrogen atom or an alkali metal atom,
or
(b) reacting a compound of the general formula

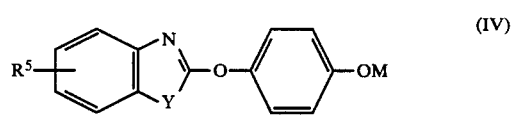

in which
R$^5$, M and Y have the meanings given above, with a compound of the general formula

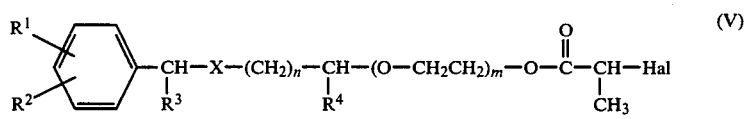

in which
R$^1$, R$^2$, R$^3$, R$^4$, X, m, n and Hal have the meanings given above,
or
(c) reacting a compound of the general formula

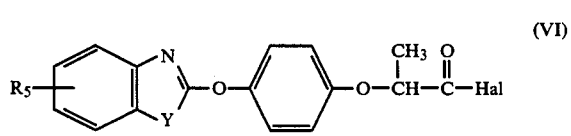

in which
R$^5$, Y and Hal have the meanings given above, with a compound of the general formula

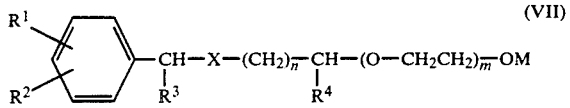 (VII)

in which
R¹, R², R³, R⁴, M, X, m and n have the meanings given above,
or
(d) reacting a compound of the general formula

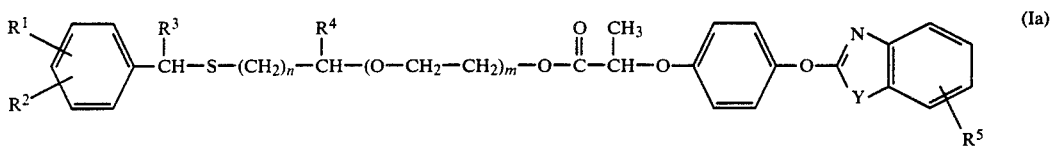 (Ia)

in which
R¹, R², R³, R⁴, R⁵, Y, m and n have the meanings given above,
with hydrogen peroxide.

The present invention also provides herbicidal compositions comprising an active ingredients substituted phenoxyalkanecarboxylic acid esters of the general formula (I). In an additional aspect, the present invention provides a method of combating weeds by applying a substituted phenoxyalkanecarboxylic acid ester of the general formula (I) to the weeds or to their habitat.

Surprisingly, the compounds according to the present invention, which have not previously been described in the literature, show an excellent herbicidal activity and are particularly useful for selectively combating a wide range of weeds, such as graminaceous weeds, without causing substantial phytotoxicity on useful farm crops, such as rice. It is particularly surprising that the compounds according to this invention also exhibit a better herbicidal activity than the ethyl-2-{4-[(6-chloro-2-benzothiazolyl)-oxy]phenoxy}-propionate, which is known from the state of art and is a closely related compound chemically and from the point of view of its action.

The compounds according to the present invention are structurally characterised by the fact that a group of the formula

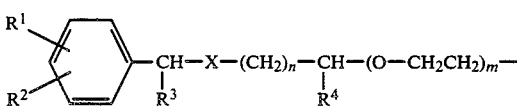

is attached to a benzo-azolyloxy-phenoxy-propionic acid moiety via an ester linkage.

Preferred compounds according to the present invention are those substituted phenoxyalkanecarboxylic acid esters of the general formula (I), in which
R¹ represents hydrogen, fluorine, chorine, bromine, iodine, alkyl with 1 to 4 carbon atoms or nitro,
R² represents hydrogen, fluorine, chlorine, bromine, iodine, alkyl with 1 to 4 carbon atoms or nitro, or R¹ and R², together with the benzene ring to which they are bonded, represent a naphthalene ring,
R³ represents hydrogen or methyl,
R⁴ represents hydrogen or methyl,
m represents 0 or 1,
n represents 1 or 2,
X represents oxygen, sulfur, sulfonyl or a group of the formula

in which
R⁶ represents alkyl with 1 to 4 carbon atoms,
R⁵ represents hydrogen, fluorine, chlorine, bromine and iodine, and
Y represents oxygen or sulfur.

Particularly preferred compounds according to the present invention are those substituted phenoxyalkanecarboxylic acid esters of the general formula (I), in which
R¹ represents hydrogen, fluorine, chlorine, bromine, methyl, ethyl, n-propyl, isopropyl, n-butyl, isobutyl, sec-butyl, tert.-butyl or nitro,
R² represents hydrogen, fluorine, chlorine, bromine, methyl, ethyl, n-propyl, isopropyl, n-butyl, isobutyl, sec-butyl, tert.-butyl or nitro, or
R¹ and R², together with the benzene ring to which they are bonded, represent a naphthalene ring,
R³ represents hydrogen or methyl,
R⁴ represents hydrogen or methyl,
m represents 0 or 1,
n represents 1 or 2,
X represents oxygen, sulfur, sulfonyl or a group of the formula

in which
R⁶ represents methyl, ethyl, n-propyl, iso-propyl, n-butyl, iso-butyl, sec-butyl or tert.-butyl,
R⁵ represents hydrogen, fluorine, chlorine, or bromine, and
Y represents oxygen or sulfur.

As already mentioned above, the compounds according to the invention contain at least one asymmetrically substituted carbon atom in the side chain, and can therefore occur in two enantiomeric forms. In the formula below, the asymmetrically substituted carbon atom is designated by an (*).

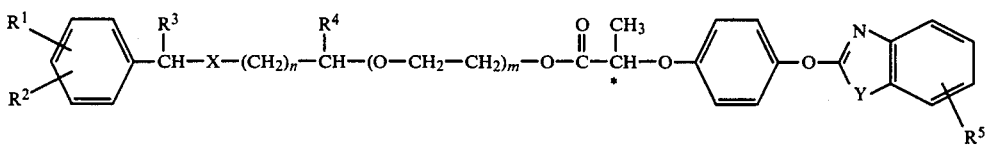

The invention relates both to the particular racemates and to the R and S enantiomers.

In the present context, R enantiomers (S enantiomers) are understood in each case as meaning those optically active compounds which have the R configuration (S configuration) at the asymmetrically substituted carbon artom of the propionic acid unit.

Particularly preferred R enantiomers are those of the substituted phenoxyalkanecarboxylic acid esters of the formula (I) in which $R^1$, $R^2$, $R^3$, $R^4$, $R^5$, X, Y, m and n have the meanings which are stated above as being particularly preferred.

The course of process variant (a) according to the present invention can be illustrated by the following general reaction scheme:

Formula (II) gives an unambiguous definition of the compounds required as starting materials in process variant (a) according to the invention. In this formula, $R^5$ and Y preferably represent those radicals which have already been mentioned as preferred therefor in connection with the description of the substances of the formula (I). Hal preferably represents chlorine or bromine.

The following may be mentioned as examples of compounds of the formula (II):
2-chlorobenzothiazole,
2-bromobenzothiazole,
2-chlorobenzoxazole,
2-bromobenzoxazole, and
6-chloro-2-bromobenzothiazole.

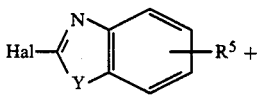

(II)

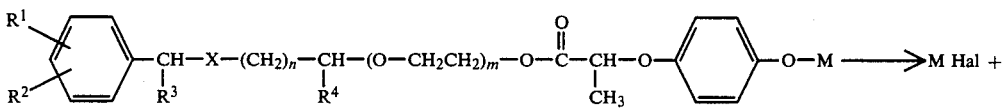

(III)

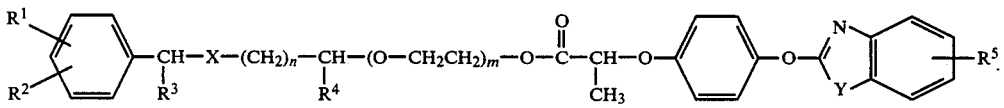

(I)

If specific starting materials are used, the course of process variant (a) according to the present invention can be represented by the following equation:

Formula (III) provides a general definition of the compounds required as further starting materials in process variant (a) according to the invention. In this

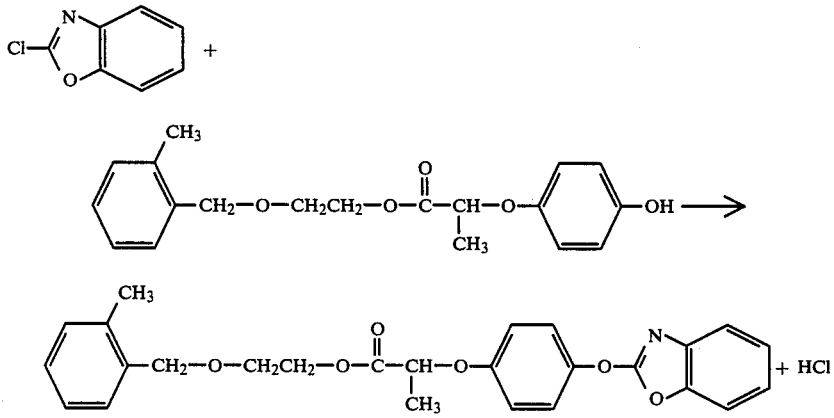

formula, $R^1$, $R^2$, $R^3$, $R^4$, X, m and n preferably represent those radicals and indices, which have already been mentioned as preferred therefor in connection with the description of the substances of the formula (I). M preferably represents a hydrogen atom, a lithium, potassium or a sodium atom.

The following may be mentioned as example of compounds of the formula (III):

2-(2-chlorobenzyloxy)ethyl 2-(4-hydroxyphenoxy)propionate,
2-(4-chlorobenzyloxy)ethyl 2-(4-hydroxyphenoxy)propionate,
2-(2,6-dichlorobenzyloxy)ethyl 2-(4-hydroxyphenoxy)propionate,
2-(2-fluorobenzyloxy)ethyl 2-(4-hydroxyphenoxy)propionate,
2-(2-methylbenzyloxy)ethyl 2-(4-hydroxyphenoxy)propionate,
2-(1-naphthylmethoxy)ethyl 2-(4-hydroxyphenoxy)propionate,
2-(3-nitrobenzyloxy)ethyl 2-(4-hydroxyphenoxy)propionate,
2-(N-benzyl-N-isopropylamino)ethyl 2-(4-hydroxyphenoxy)-propionate,
2-benzyloxyethyl 2-(4-hydroxyphenoxy)propionate,
2-(α-methylbenzyloxy)ethyl 2-(4-hydroxyphenoxy)propionate,
2-(2-benzyloxyethoxy)ethyl 2-(4-hydroxyphenoxy)propionate,
2-(1-methyl-2-benzyloxy)ethyl 2-(4-hydroxyphenoxy)-propionate,
3-benzyloxypropyl 2-(4-hydroxyphenoxy)propionate,
2-benzylthioethyl 2-(4-hydroxyphenoxy)propionate,
2-(2-chlorobenzylthio)ethyl 2-(4-hydroxyphenoxy)propionate,
2-(2-chlorobenzylsulfonyl)ethyl 2-(4-hydroxyphenoxy)-propionate, and
2-(N-benzyl-N-methylamino)ethyl 2-(4-hydroxyphenoxy)-propionate, Reaction variant (a) according to the present invention is preferably carried out in the presence of a solvent or diluent. For this purpose, any inert solvents and diluents may be employed.

Examples of such solvents and diluents include water; aliphatic, alicyclic and aromatic hydrocarbons —each of which may optionally be chlorinated (such as hexane, cyclohexane, petroleum ether, ligroin, benzene, toluene, xylene, methylene chloride, chloroform, carbon tetrachloride, ethylene chloride, tri-chloroethylene, and chlorobenzene), ethers (such as diethyl ether, methyl ethyl ether, di-isopropyl ether, di-butyl ether, propylene oxide, dioxane, and tetrahydrofuran), ketones (such as acetone, methyl ethyl ketone, methyl isopropyl ketone, and methyl isobutyl ketone, nitriles (such as acetonitrile, propionitrile, and acrylonitrile), alcohols (such as methanol, ethanol, iso-propanol, butanol, and ethylene glycol), esters (such as ethyl acetate and amyl acetate), acid amides (such as dimethylformamide and dimethylacetamide), sulfones and sulfoxides (such as dimethylsulfoxide and sulfolane) and bases (such as pyridine).

The reaction variant (a) is preferably carried out in the presence of acid-binding agent. As examples of such acid-binding agents, there may be mentioned hydroxides, carbonates, bicarbonates and alcoholates of alkali metals, and tertiary amines such as triethylamine, diethylaniline, pyridine, Reaction variant (a) can be carried out over a wide range of temperatures. Generally, it is carried out at a temperature between −20° C. and the boiling point of the reaction mixture, preferably between 0° C. and 100° C.

This reaction variant (a) is preferably carried out under ambient pressure, although it can be effected under elevated or reduced pressure.

The course of process variant (b) according to the present invention can be illustrated by the following general reaction scheme:

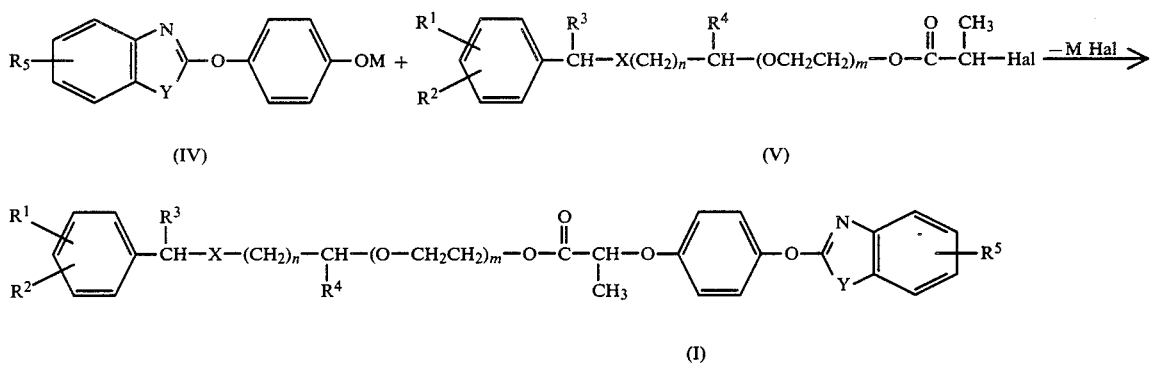

and the corresponding lithium, sodium and potassium salts.

If specific starting materials are used, the course of process variant (b) according to the present invention can be represented by the following equation:

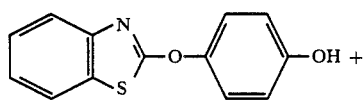

-continued

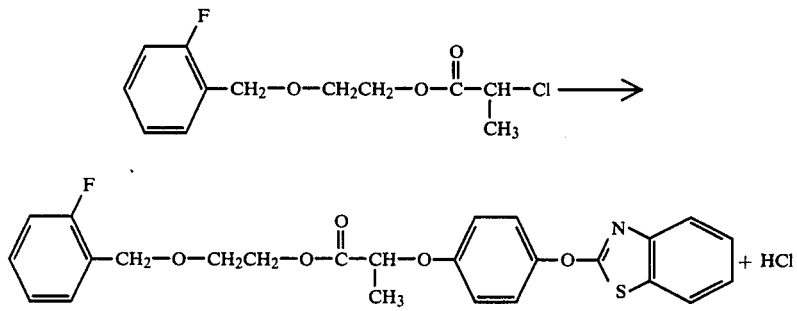

Formula (IV) gives an unambiguous definition of the compounds, which are required as starting materials in process variant (b) according to the invention. In this formula, $R^5$ and Y preferably represent those radicals which have already been mentioned as preferred therefor in connection with the description of the substances of the formula (I). M preferably represents a hydrogen atom, a lithium, potassium or a sodium atom.

Formula (V) provides a general definition of the compounds, which are also required as starting materials in process variant (b) according to the invention. In this formula, $R^1$, $R^2$, $R^3$, $R^4$, X, m and n preferably represent those radicals and indices, which have already been mentioned as preferred therefor in connection with the description of the substances of the formula (I).

products with high purity in high yield. Likewise, reaction variant (b) is preferably carried out in the presence of an acid binding agent as described hereinbefore for reaction variant (a).

Reaction variant (b) can be carried out over a wide range of temperatures. Generally, it is carried out at a temperature between $-20°$ C. and the boiling point of the reaction mixture, preferably between $0°$ C. and $100°$ C.

The reaction variant (b) is preferably carried out under ambient pressure, although it can be effected under elevated or reduced pressure.

The course of process variant (c) according to the pesent invention can be illustrated by the following general reaction scheme:

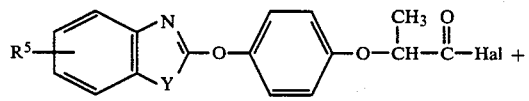

(VI)

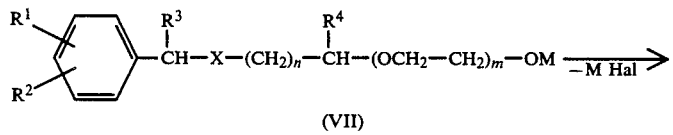

(VII)

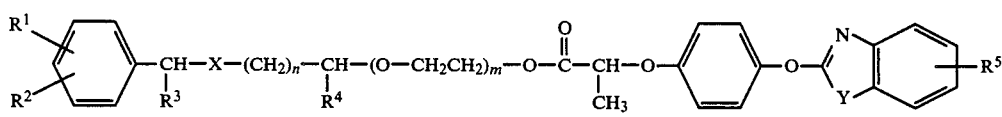

(I)

Hal preferably represents chlorine or bromine.

In carrying out reaction variant (b), any of the inert solvents or diluents as described hereinbefore for reaction variant (a) are preferably used to obtain the end If specific starting materials are used, the course of process variant (c) according to the present invention can be represented by the following equation:

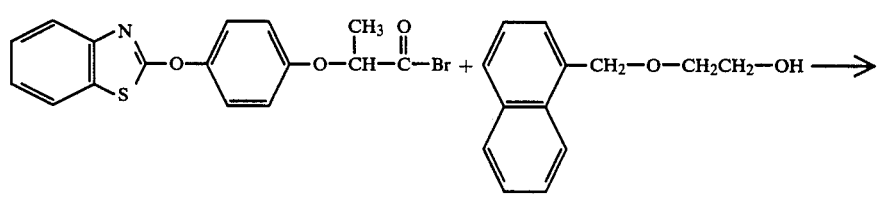

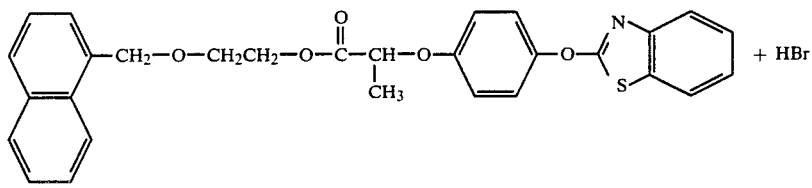

Formula (VI) gives an unambiguous definition of the compounds required as starting materials in process variant (c) according to the invention. In this formula, $R^5$ and Y preferably represent those radicals which have already been mentioned as preferred therefor in connection with the description of the substances of the formula (I). Hal preferably represents chlorine or bromine.

the reaction mixture, preferably between 0° C. and 100° C.

The reaction variant (c) is preferably carried out under ambient pressure, although it can be effected under elevated or reduced pressure.

The course of process variant (d) according to the present invention can be illustrated by the following general reaction scheme:

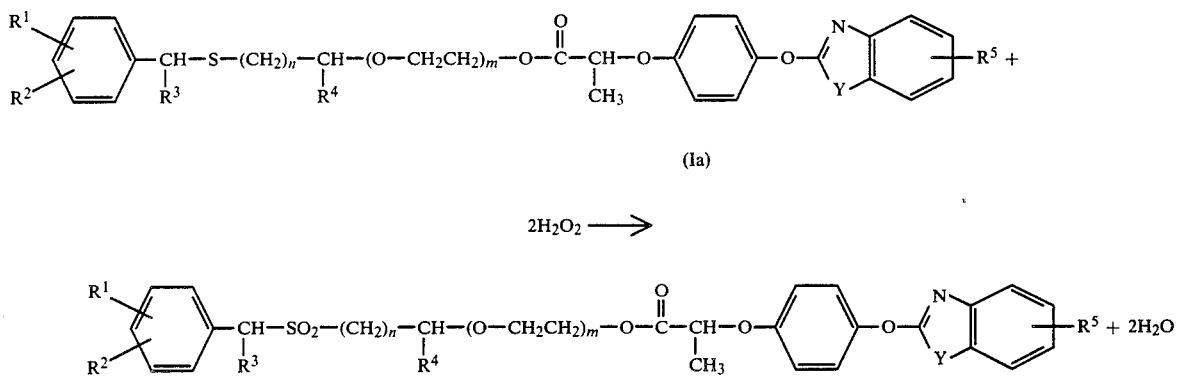

Formula (VII) provides a general definition of the compounds required as further starting materials in process variant (c) according to the invention. In this formula, $R^1$, $R^2$, $R^3$, $R^4$, X, m and n preferably represent those radicals and indices, which have already been mentioned as preferred therefor in connection with the description of the substances of the formula (I). M preferably represents a hydrogen atom, a lithium, sodium or a potassium atom.

In carrying out reaction variant (c), any of the inert solvents or diluents as described hereinbefore for reaction variant (a), except alcohols, are preferably used to obtain the end products with high purity in high yield. Likewise, reaction variant (c) is preferably carried out in the presence of an acid-binding agent as described hereinbefore for reaction variant (a).

Reaction variant (c) can be carried out over a wide range of temperatures. Generally, it is carried out at a temperature between −20° C. and the boiling point of If specific starting materials are used, the course of process variant (d) according to the present invention can be represented by the following equation:

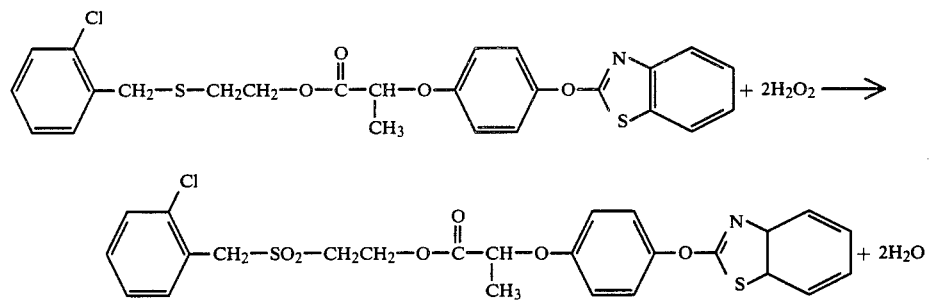

In carrying out reaction variant (d), any of the inert solvents or diluents as described hereinbefore for reaction variant (a) can be used.

Reaction variant (d) can be carried out over a wide range of temperatures. Generally, it is carried out at a temperature between −20° C. and the boiling point of the reaction mixture, preferably between 0° C. and 100° C.

The reaction variant (d) is preferably carried out under ambient pressure, although it can be effected under elevated or reduced pressure.

The active compounds of the formula (I) according to the present invention show excellent selective herbicidal activity. They can be applied either before or after emergence of the plants. They are preferably applied before emergence of the plants, that is to say by the pre-emergence method. They can also be incorporated into the soil before sowing.

Since the active compounds according to the present invention show little or no toxicity towards warm-blooded animals and show good selectivity for agricultural plants, that is, cause no phytotoxicity for agricultural plants, they can be conveniently used as herbicides for controlling weeds, particularly for the control of graminaceous weeds. By "weeds" in the broadest sense there are meant plants growing in places where they are not desired.

The active compounds according to the present invention may be used, for example, co combat the following plants:
Echinochloa crus-galli P. Beauv. var. oryzicola Ohwi,
Echinochloa crus-galli P. Beauv. var. caudata Kitagawa,
Echinochloa crus-galli P. Beauv. var. formosensis Ohwi,
Sacciolepis indica Chase var. oryzetorum Ohwi,
Glyceria acutiflora torr.,
Glyceria natans Komorov.,
Polypogon fugax Steud.,
Panicum bisulcatum Thunb., and
Paspalum distichum L.,
Echinochloa crus-galli P. Beauv.,
Agropyron tsukushiense Ohwi var. transiens Ohwi,
Poa annua L.,
Alopecurus aequalis Sobol. var. amurensis Ohwi,
Eleusine indica Gaertn.,
Digitaria adscendens Henr.,
Cynodon dactylon Pers.,
Setaria viridis P. Beauv.,
Setaria glauca P. Beauv., and
Avena fatua L.

In addition, they also show excellent herbicidal and regrowth-control effects on, for example, perennial weeds, such as Johnson grass and Cynodon dactylon.

The active compounds according to the present invention may be used as selective herbicides in many cultures. As examples the following cultures may be mentioned: beans, cotton, carrot, potato, beet, cabbage, mustard, peanut, radish, tobacco, tomato and cucumber.

The active compounds according to the present invention can be converted into customary formulations using agricultural acceptable adjuvants by methods generally practiced in the production of agricultural chemicals, In actual use, the herbicidal compositions in various forms are applied either directly or after diluting them with water to the desired concentrations. Examples of the agricultural acceptable adjuvants, as referred to herein, are diluents (solvents, extenders, carriers), surfaceactive agents (solubilizing agents, emulsifiers, dispersants, wetting agents), stabilizers, stickers, aerosol propellants, and synergists.

Examples of the solvents are water, and organic solvents, for example hydrocarbons (e.g., n-hexane, petroleum ether, naphtha, petroleum fractions (e.g. paraffin waxes, kerosine, light oils, middle oils, heavy oils), benzene, toluene, and xylenes), halogenated hydrocarbons (e.g. methylene chloride, carbon tetrachloride, trichloroethylene, ethylene dichloride, chlorobenzene and chloroform), alcohols (e.g. methyl alcohol, ethyl alcohol, propyl alcohol, and ethylene glycol), ethers (e.g., ethyl ether, ethylene oxide and dioxane), alcohol ethers (e.g., ethylene glycol monomethyl ether), ketones (e.g. acetone and isophorone), esters (e.g., ethyl acetate and amyl acetate), amides (e.g. dimethylformamide and dimethylacetamide) and sulfoxides (e.g., dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophylite, talc, montmorillonite, beidelite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acid salts (e.g., alkylarylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylenne glycol ethers (e.g. polyoxyethylene alkylaryl ethers and the condensation products thereof), polyoxyethylene glycol esters (e.g., polyoxyethylene fatty acid esters), and polyhydric alcohol esters (e.g. polyoxyethylene sorbitan monolaurate); and amphoteric surface-active agents.

Examples of other adjuvants include stabilizers; stickers (e.g. agricultural soaps, casein lime, sodium alginate, polyvinayl alcohols, vinyl acetate-type adhesives and acrylic adhesives); aerosol propellants (such as trichlorofluoromethane, dichlorofluoromethane, 1,2,2-trichloro-1,1,2-trifluoromethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers (such as casein, tragacanth, carboxymethyl cellulose (CMC), and polyvinyl alcohol (PVA); and synergists.

The active compounds according to this invention can be converted into the customary formulations, such as emulsifiable concentrates, oils, wettable powders, soluble powders, suspensions, dusts, granules and pulverulent compositions. These formulations may be produced in known manner.

The amount of active compound in ready-to-use preparations can vary widely according to circumstance. However, it is in general from 0.001 to about 100 percent by weight of active compound, preferably from about 0.005 to 95 percent by weight.

In actual use, the suitable amount of the active compound in the aforesaid compositions of various forms and ready-to-use preparations is, for example, about 0.01 to about 95% by weight, preferably about 0.05 to about 60% by weight.

The content of the active ingredient can be properly varied depending upon the form of the preparation or composition, the method, purpose, time and locus of its application, the state of occurrence of weeds, etc.

If required, the compound of this invention may be used further in combination with other agricultural chemicals, for example insecticides, fungicides, miticides, nematocides, antiviral agents, other herbicides, plant growth regulators and attractants (e.g. organophosphorus ester compounds, carbamate compounds, dithio (or thiol) carbamate compounds, organic chlorine compounds, dinitro compounds, organic sulfur or organo metallic compounds, antibiotics, substituted diphenyl ether compounds, urea, compounds, and triazine compounds), and/or fertilizers.

Various compositions and ready-to-use preparations containing the aforesaid active ingredients can be applied by various methods generally practiced in the field of agricultural chemical application, for example dispersing (liquid spraying, misting, atomizing, dust dispersing, granule dispersing, water surface application and pouring); and soil application (mixing with the soil, and sprinkling). They can also be used by the so-called ultralow volume spraying method. According to this method, the active ingredient may be included in an amount of 100%.

The rate of application per unit area is, for example, about 0.1 to about 5.0 kg, preferably about 0.2 to about 2.0 kg, per hectare. In special cases, however, it may, and sometimes should, be outside the specified range.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds or to a habitat thereof, a compound of the present invention alone or in the form of a composition containing as active ingredient a compound of the present invention in admixture with a diluent or carrier.

It will be seen that the usual methods of providing a harvested crop may be improved by the present invention.

The following examples illustrate the present invention specifically. It should be noted, however, that the invention is not limited to these specific examples alone.

PREPARATIVE EXAMPLES

Example 1

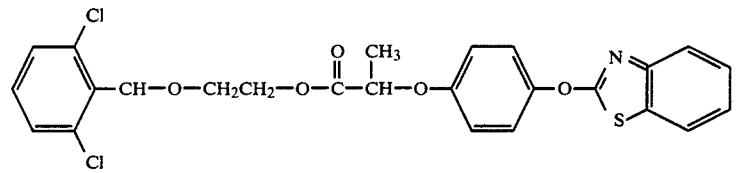

38.5 g of 2-(2,6-dichlorobenzyloxy)ethyl 2-(4-hydroxyphenoxy)-propionate were dissolved in 200 ml of dimethylformamide and 15.2 g of potassium carbonate were added to the solution. The mixture was stirred at 80° C. for 1 hour. A solution of 18.6 g of 2-chlorobenzothiazole in 50 ml of dimethylformamide was added dropwise at this temperature to the resulting mixture. After the addition, the mixture was stirred at the same temperature for 2 hours to complete the reaction. The reaction mixture was poured onto ice water, and the separated oily product was extracted with toluene. The toluene layer was washed successively with a 1% aqueous solution of sodium hydroxide and water, and then toluene was evaporated under reduced pressure to give 43.5 g of 2-(2,6-dichlorobenzyloxy)ethyl 2-[4-(benzothiazol-2-yloxy)pheoxy]propionate as a viscous oily product represented by the formula above.

$n_D^{25} = 1.6125$.

In substantially the same manner as described in Example 1, there were obtained the compounds according to the invention which are shown in the following Table 1.

TABLE 1

| Compound No. | R¹ | R² | R³ | X | n | R⁴ | m | Y | R⁵ | Physical constant |
|---|---|---|---|---|---|---|---|---|---|---|
| 2 | 2-Cl | H | H | O | 1 | H | 0 | O | H | $n_D^{25}1.5670$ |
| 3 | 4-Cl | H | H | O | 1 | H | 0 | O | H | $n_D^{25}1.5665$ |
| 4 | 2-Cl | 6-Cl | H | O | 1 | H | 0 | O | H | $n_D^{25}1.5915$ |
| 5 | 2-F | H | H | O | 1 | H | 0 | O | H | $n_D^{25}1.5460$ |
| 6 | 2-CH₃ | H | H | O | 1 | H | 0 | O | H | $n_D^{20}1.5535$ |
| 7 | 3-NO₂ | H | H | O | 1 | H | 0 | O | H | $n_D^{25}1.5750$ |
| 8 | H | H | H | —N—CH(CH₃)₂ | 1 | H | 0 | O | H | $n_D^{25}1.5560$ |
| 9 | H | H | H | O | 1 | H | 0 | S | H | $n_D^{25}1.5863$ |
| 10 | H | H | H | O | 1 | H | 0 | S | 6-Cl | $n_D^{25}1.5903$ |
| 11 | 2-F | H | H | O | 1 | H | 0 | S | H | $n_D^{25}1.5840$ |
| 12 | 2-Cl | 6-Cl | H | O | 1 | H | 0 | S | H | $n_D^{25}1.6135$ |
| 13 | H | H | —CH₃ | O | 1 | H | 0 | S | H | $n_D^{25}1.586$ |
| 14 | H | H | H | O | 1 | H | 1 | S | H | $n_D^{25}1.5750$ |
| 15 | H | H | H | O | 1 | —CH₃ | 0 | S | H | $n_D^{25}1.5872$ |
| 16 | H | H | H | O | 2 | H | 0 | S | H | $n_D^{25}1.5820$ |
| 17 | H | H | H | S | 1 | H | 0 | S | H | $n_D^{25}1.6130$ |
| 18 | 2-Cl | H | H | S | 1 | H | 0 | S | H | $n_D^{25}1.6192$ |
| 19 | 2-Cl | H | H | —SO₂— | 1 | H | 0 | S | H | $n_D^{25}1.6300$ |

TABLE 1-continued

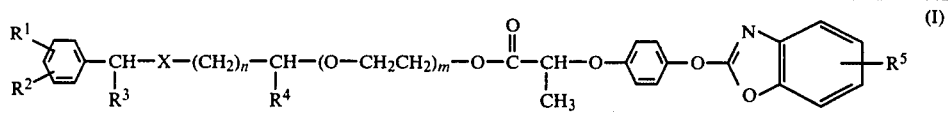

| Compound No. | R¹ | R² | R³ | X | n | R⁴ | m | Y | R⁵ | Physical constant |
|---|---|---|---|---|---|---|---|---|---|---|
| 20 | H | H | H | —N(CH₃)— | 1 | H | 1 | S | H | $n_D^{25} 1.5910$ |
| 21 | H | H | H | —N—CH(CH₃)₂ | 1 | H | 1 | S | H | $n_D^{25} 1.5918$ |
| 22 | naphthyl | | H | O | 1 | H | 0 | O | H | $n_D^{25} 1.5995$ |
| 23 | naphthyl | | | H | O | 1 | H | 0 | S | H | $n_D^{25} 1.6226$ |

In the following Examples, the compounds according to the present invention are each identified by the number of the corresponding preparative Example. References to "parts" are to be understood as meaning parts by weight.

Example 2

(Wettable powder)

Fifteen parts of compound No. 6 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto weeds and/or their habitat.

Example 3

(Emulsifiable concentrate)

Thirty parts of compound No. 11 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto weeds and/or their habitat.

Example 4

(Dust)

Two parts of compound No. 5 of the invention and 98 parts of powdery clay are pulverized and mixed to form a dust. It is scattered over weeds and/or their habitat.

Example 5

(Granules)

25 parts of water are added to a mixture consisting of 10 parts of compound No. 8 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds and/or their habitat.

Example 6

(Granules)

Ninety-five parts of clay mineral particles having a particle size distribution between 0.2 and 2 mm are put in a rotary mixer, and with rotation, 5 parts of the oily compound No. 15 of the invention is sprayed onto the particles to wet them uniformly to form granules. The granules are scattered over weeds and/or their habitat.

The herbicidal activity of the compounds of the formula (I) is illustrated by the following biotest Example.

The known comparison compound is identified as follows:

Comparison (A-1)

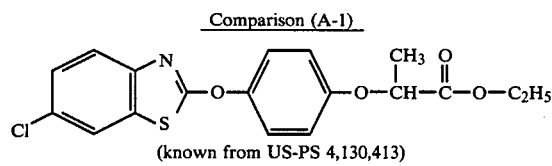

(known from US-PS 4,130,413)

Example 7

(Biological test)

Test of foliar/soil treatment of aquatic paddy weeds under irrigation (pot test):

Formulation of an active compound

Carrier: 5 parts by weight of acetone
Emulsifier: 1 part by weight of benzyloxyglycol ether A preparation containing the active compound is formed by mixing 1 part by weight of each of the active compounds with the carrier and emulsifier in the amounts indicated above, and diluting a predetermined amount of the resulting emulsifiable concentrate with water.

Testing procedure

Aquatic paddy soil was filled in Wagner pots (1/5,000 ares), and rice seedlings (variety: Kinnampu) in the 2- to 3-leaf stage (plant height about 10 cm) were transplanted at a rate of 2 per pot. Seeds of *Echinochloa Crus-galli* P. Beauv. var oryzicola Ohwi, *Echinochloa crus-galli* P. Beauv. var. caudata Kitagawa, *Sacciolepis indica* Chase var. oryzetorum Ohwi and *Panicum bisul-*

*catum* Thunb. were inoculated in the pots. The soil in the pots was maintained in the wet state. After *Echinochloa crus-galli* P. Beauv. var. *oryzicola* Ohwi grew to a stage of approximately two leaves (about 7 to 9 days after sowing), each pot was watered to a depth of about 6 cm. A predetermined amount of the compound of this invention in the form of an emulsion was applied by means of a pipette to treat each pot. After the treatment, the pots were subjected to a water leaking treatment for 2 days at a rate of 2 to 3 cm per day, and thereafter maintained in the watered state to a depth of about 3 cm. Four weeks after the treatment the herbicidal effect and the degree of phytotoxicity were evaluated on a scale of from 0 to 5 as follows:

Evaluation of the herbicidal effect (herbicidal rate based on the non-treated area):
5: at least 95% (withered)
4: at least 80% but less than 95%
3: at least 50% but less than 80%
2: at least 30% but less than 50%
1: at least 10% but less than 30%
0: less than 10% (no effect)

Evaluation of phytotoxicity to aquatic rice plants (the phytotoxicity rate based on the non-treated area):
5: at least 90% (fatal injury)
4: at least 50% but less than 90%
3: at least 30% but less than 50%
2: at least 10% but less than 30%
1: more than 0% but less than 10%
0: 0% (no phytotoxicity)

The test results are shown in Table 2.

TABLE 2

| Amount of the active ingredient (kg/ha) | Herbicidal effect | | | | Phytotoxicity to rice |
|---|---|---|---|---|---|
| | A | B | C | D | |
| Compound No. | | | | | |
| 1  1.0 | 5 | 5 | 5 | 5 | 0 |
| 5  1.0 | 5 | 5 | 5 | 5 | 0 |
| 6  1.0 | 5 | 5 | 5 | 5 | 0 |
| 11  1.0 | 5 | 5 | 5 | 5 | 0 |
| 12  1.0 | 5 | 5 | 5 | 5 | 0 |
| 15  0.5 | 5 | 5 | 5 | 5 | 0 |
| 16  0.5 | 5 | 5 | 5 | 5 | 0 |
| 18  1.0 | 5 | 5 | 5 | 5 | 0 |
| 21  1.0 | 5 | 5 | 5 | 5 | 0 |
| Comparison | | | | | |
| A-1  1.0 | 5 | 5 | 5 | 5 | 4 |
| 0.5 | 5 | 5 | 5 | 5 | 3 |

TABLE 2-continued

| Amount of the active ingredient (kg/ha) | Herbicidal effect | | | | Phytotoxicity to rice |
|---|---|---|---|---|---|
| | A | B | C | D | |
| 0.1 | 3 | 3 | 4 | 4 | 2 |

A: *Echinochloa crus-galli* P. Beauv. var. *oryzicola* Ohwi,
B: *Echinochloa crus-galli* P. Beauv. var. *caudata* Kitagawa,
C: *Sacciolepis indica* Chase var. *oryzetorum* Ohwi,
D: *Panicum bisulcatum* Thunb.

What is claimed is:

1. A method of combating weeds in the cultivation of rice in a field which comprises applying to such rice field a weed-herbicidally effective amount of a phenoxyalkanecarboxylic acid ester of the formula

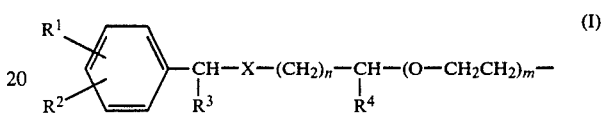

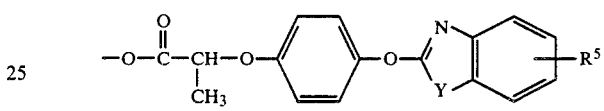

in which
$R^1$ and $R^2$, independently of one another, represent a hydrogen atom, a halogen atom, a lower alkyl group or a nitro group, or
$R^1$ and $R^2$, together with the benzene ring to which they are bonded, represent a naphthalene ring,
$R^3$ and $R^4$, independently of one another, represent a hydrogen atom or a methyl group,
n represents 1 or 2,
m represents 0 or 1,
X represents an oxygen atom, a sulfur atom, a sulfonyl group, or a group of the formula

in which
$R^6$ represents a lower alkyl group,
$R^5$ represents a hydrogen atom or a halogen atom, and
Y represents an oxygen atom or a sulfur atom.

2. A method as claimed in claim 1, wherein said phenoxyalkanecarboxylic acid ester is selected from the compounds of the formulae

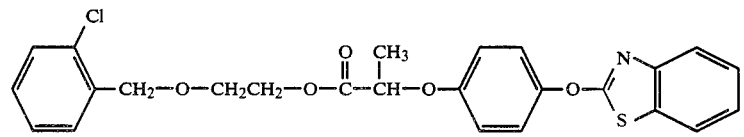

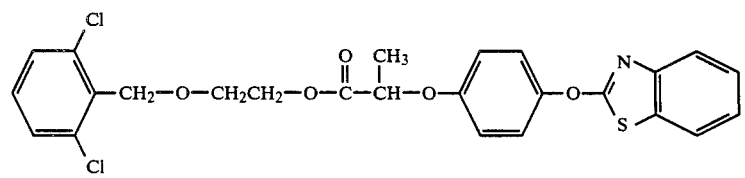

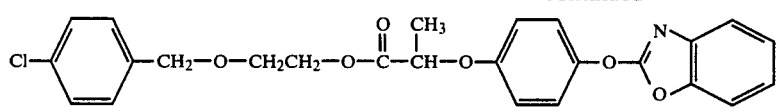
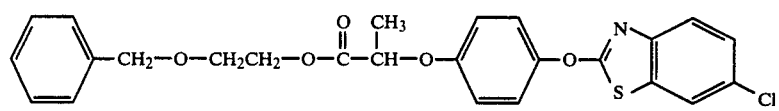
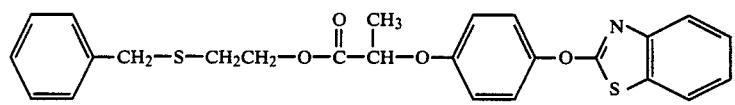
and
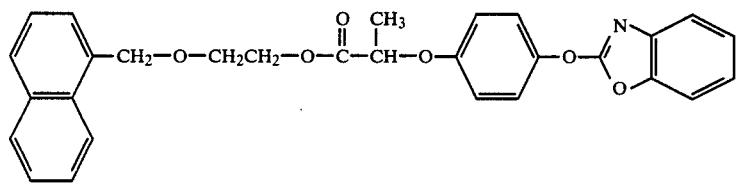

UNITED STATES PATENT AND TRADEMARK OFFICE
CERTIFICATE OF CORRECTION

PATENT NO. : 4,666,503

DATED : May 19, 1987

INVENTOR(S) : Kozo Shiokawa, et al.

Page 1 of 2

It is certified that error appears in the above-identified patent and that said Letters Patent are hereby corrected as shown below:

| | |
|---|---|
| Col. 3, line 33 | Before "active" delete "an" and substitute --as-- |
| Col. 5, line 15 | Delete "artom" and substitute --atom-- |
| Col. 7, line 7 | Delete "example" and substitute --examples-- |
| Col. 10, line 29 | Delete "pesent" and substitute --present-- |
| Col. 12, line 34 | After "formula Insert --(Ib)-- |
| Col. 14, line 23 | Correct spelling of --polyoxyethylene-- |
| Col. 14, line 31 | Correct spelling of --polyvinyl-- |

UNITED STATES PATENT AND TRADEMARK OFFICE
CERTIFICATE OF CORRECTION

PATENT NO. : 4,666,503

DATED : May 19, 1987

INVENTOR(S) : Kozo Shiokawa, et al.

It is certified that error appears in the above-identified patent and that said Letters Patent is hereby corrected as shown below:

Col. 16, line 45     End of formula delete "  "

and substitute -- 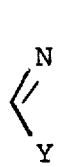 --

Signed and Sealed this

Nineteenth Day of January, 1988

*Attest:*

DONALD J. QUIGG

*Attesting Officer*    *Commissioner of Patents and Trademarks*